United States Patent
DeCesare et al.

(10) Patent No.: US 7,970,865 B2
(45) Date of Patent: Jun. 28, 2011

(54) DATA RETRIEVAL METHOD AND SYSTEM

(75) Inventors: Donna DeCesare, Charlotte, NC (US); Daniel Joseph Gatins, Atlanta, GA (US); Richard Hennessy, Austin, TX (US); Julian I. Kamil, Gaithersburg, MD (US); Gerald McLoughlin, Southbury, CT (US); William Philip Shaouy, Atlanta, GA (US)

(73) Assignee: International Business Machines Corporation, Armonk, NY (US)

( * ) Notice: Subject to any disclaimer, the term of this patent is extended or adjusted under 35 U.S.C. 154(b) by 149 days.

(21) Appl. No.: 12/432,853

(22) Filed: Apr. 30, 2009

(65) Prior Publication Data

US 2010/0281137 A1    Nov. 4, 2010

(51) Int. Cl.
*G06F 15/16* (2006.01)

(52) U.S. Cl. ............... 709/218; 709/217; 705/2

(58) Field of Classification Search .......... 709/218, 709/217, 219, 201–203; 715/700–866; 705/2–6
See application file for complete search history.

(56) References Cited

U.S. PATENT DOCUMENTS

| | | | |
|---|---|---|---|
| 5,832,447 A | 11/1998 | Rieker et al. | |
| 6,692,436 B1 | 2/2004 | Bluth et al. | |
| 7,376,677 B2 | 5/2008 | Ober et al. | |
| 2003/0236682 A1* | 12/2003 | Heyer | 705/2 |
| 2006/0122863 A1* | 6/2006 | Gottesman et al. | 705/2 |
| 2008/0270180 A1 | 10/2008 | Sholtis et al. | |
| 2008/0312959 A1 | 12/2008 | Rose et al. | |
| 2008/0319271 A1 | 12/2008 | Barnowski et al. | |
| 2009/0024416 A1* | 1/2009 | McLaughlin et al. | 705/3 |

FOREIGN PATENT DOCUMENTS

WO    WO2009005372 A1    1/2009

* cited by examiner

*Primary Examiner* — Wing F Chan
*Assistant Examiner* — Ruolei Zong
(74) *Attorney, Agent, or Firm* — Schmeiser, Olsen & Watts; Anna L. Linne

(57) ABSTRACT

A data retrieval method and system. The method includes transmitting, by a computing device to data source organizations in response to a request for data, a request for populating online forms. The computing device receives input data associated with the online forms. The computing device transmits notification data requesting analysis of the input data and an input form for uploading results of the analysis. The computing device receives analysis data files. The computing device transmits the analysis data files and data transformation requirements to an IT service organization. The computing device receives clarification inquiries data. The computing device transmits the clarification inquiries data to the data source organizations. The computing device receives response data from the data source organizations. The computing device receives modified analysis data files from the IT service organization. The computing device transmits notification data indicating results of the modified analysis data files to an entity.

14 Claims, 5 Drawing Sheets

| A | B | C | D | E | F | G | H | I | J |
|---|---|---|---|---|---|---|---|---|---|
| Source | Subject Area | Type of Record | Long Term Care # | Matches LIC # | Provider # | Matches Medical ID | Facility Name | Room Rate | Leave Rate |
| HITT | Nursing Home | Charge | LTC1038 | #N/A | 000407 | 000407 | Hosp. | 145.13 | 99.69 |
| HITT | Nursing Home | Charge | LTC1059 | #N/A | 000595 | 000595 | Memorial Center | 138.17 | 94.47 |
| HITT | Nursing Home | Charge | LTC1001D | #N/A | 001400 | 00014009 | Nursing Home A | 137.90 | 94.27 |
| HITT | Nursing Home | Charge | LTC1001E | #N/A | 001402 | #N/A | Center A | 133.76 | 91.16 |
| HITT | Nursing Home | Charge | LTC1069W | #N/A | 001410 | #N/A | Center West | 151.96 | 104.81 |
| HITT | Nursing Home | Charge | LTC1069N | #N/A | 001420 | 001420 | Center North | 157.28 | 108.80 |
| HITT | Nursing Home | Charge | LTC1101H | #N/A | 001420A | 001420A | Center B | 137.96 | 94.31 |
| HITT | Nursing Home | Charge | LTC1101L | #N/A | 001424A | 001424 | Nursing Home B | 137.07 | 93.65 |
| HITT | Nursing Home | Charge | LTC1148F | #N/A | 0014244A | #N/A | Nursing Home C | 168.38 | 117.13 |
| HITT | Nursing Home | Charge | LTC1148G | #N/A | 000407 | 001427 | Care Center A | 162.85 | 112.98 |
| HITT | Nursing Home | Charge | LTC1059 | #N/A | 002204 | 002204 | Healthcare Center D | 132.10 | 89.92 |

*FIG. 3*

| HITT TAB | HITT TYPE | SP_OCCUP_THERAPY | SP_PHYSICAL_THERAPY | SP_SPEECH_PATH | TOT_EMPLOYEES | ACUTE_RESPITE | SP_COUNSELING | SP_HOME_HEALTH_AIDE | SP_HOME-MAKER | SP_MEDICAL_SOCIAL | SP_MEDICAL_SUPPLIES | SP_SHORT_TERM_CARE |
|---|---|---|---|---|---|---|---|---|---|---|---|---|
| 28 | 29 | 32 | 33 | 34 | 35 | 56 | 57 | 58 | 59 | 60 | 61 | 62 |
| LONG TERM CARE | A | 2 | 2 | 2 | 101 | Y | Y | Y | Y | Y | Y | Y |
| LONG TERM CARE | A | 2 | 2 | 2 | 101 | Y | Y | Y | Y | Y | Y | Y |
| LONG TERM CARE | A | Y | Y | Y | 26 | Y | Y | Y | Y | Y | Y | Y |
| LONG TERM CARE | A | 2 | 2 | 2 | 61 | Y | Y | Y | Y | Y | Y | Y |
| LONG TERM CARE | A | 2 | 2 | 2 | 84 | Y | Y | Y | N | Y | Y | Y |
| LONG TERM CARE | A | 2 | 2 | 2 | 13 | Y | Y | Y | N | Y | Y | Y |
| LONG TERM CARE | A | Y | Y | Y | 14 | Y | Y | Y | Y | Y | Y | Y |
| LONG TERM CARE | A | 2 | 2 | 2 | 36 | Y | Y | Y | N | Y | Y | Y |
| LONG TERM CARE | A | 2 | 2 | 2 | 26 |  | Y | Y | Y | Y | Y | Y |
| LONG TERM CARE | A | 2 | 2 | 2 | 32 |  | Y | Y | Y | Y | Y | Y |
| LONG TERM CARE | A | 2 | 2 | 2 | 107 | Y |  | Y | N | Y | Y | Y |
| LONG TERM CARE | A | 2 | 2 | 2 | 10 | Y | Y | Y | Y | N | Y | N |
| LONG TERM CARE | A | 2 | 2 | 2 | 14 | Y | Y | Y | N | Y | Y | N |
| LONG TERM CARE | A | Y | Y | Y | 4 | Y | Y | Y | Y | Y | Y | Y |
| LONG TERM CARE | A | 2 | Y | 2 | 5 | Y | Y | Y | N | Y | Y | Y |
| LONG TERM CARE | A | 2 | 2 | 2 | 8 | Y | Y | Y | Y | Y | Y | Y |

DATA RETRIEVAL METHOD AND SYSTEM

FIELD OF THE INVENTION

The present invention relates to a method and associated system for gathering and analyzing data from multiple sources.

BACKGROUND OF THE INVENTION

Retrieving information from multiple parties typically comprises a complicated and inefficient process with little flexibility. A first party requesting specified information may not receive the specified information in a timely manner.

SUMMARY OF THE INVENTION

The present invention provides a data retrieval method comprising:

receiving, by a computing device from a first entity, a first request for data;

transmitting, by said computing device to a plurality of data source organizations in response to said first request, a second request for populating a plurality of online forms;

receiving, by said computing device from said data source organizations in response to said second request, input data associated with said online forms;

executing, by a computer processor of said computing device, a state change associated with said input data;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data;

transmitting, by said computing device to said data source organizations, said clarification inquiries data;

receiving, by said computing device from said data source organizations, response data associated with said clarification inquiries data;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

The present invention provides a computing device comprising a processor coupled to a computer-readable memory unit, said memory unit comprising instructions that when executed by the processor implement a data retrieval method, said method comprising:

receiving, by said computing device from a first entity, a first request for data;

transmitting, by said computing device to a plurality of data source organizations in response to said first request, a second request for populating a plurality of online forms;

receiving, by said computing device from said data source organizations in response to said second request, input data associated with said online forms;

executing, by a computer processor of said computing device, a state change associated with said input data;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data;

transmitting, by said computing device to said data source organizations, said clarification inquiries data;

receiving, by said computing device from said data source organizations, response data associated with said clarification inquiries data;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

The present invention provides a computer program product, comprising a computer readable medium comprising a computer readable program code embodied therein, said computer readable program code adapted to implement a data retrieval method within a computing device comprising a computer-readable memory unit, said method comprising:

receiving, by said computing device from a first entity, a first request for data;

transmitting, by said computing device to a plurality of data source organizations in response to said first request, a second request for populating a plurality of online forms;

receiving, by said computing device from said data source organizations in response to said second request, input data associated with said online forms;

executing, by a computer processor of said computing device, a state change associated with said input data;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data;

transmitting, by said computing device to said data source organizations, said clarification inquiries data;

receiving, by said computing device from said data source organizations, response data associated with said clarification inquiries data;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

The present invention provides a process for supporting computer infrastructure, said process comprising providing at least one support service for at least one of creating, integrating, hosting, maintaining, and deploying computer-readable code in a computing device comprising a computer-readable memory unit, wherein the code in combination with the computing device is capable of performing a data retrieval method, said method comprising:

receiving, by said computing device from a first entity, a first request for data;

transmitting, by said computing device to a plurality of data source organizations in response to said first request, a second request for populating a plurality of online forms;

receiving, by said computing device from said data source organizations in response to said second request, input data associated with said online forms;

executing, by a computer processor of said computing device, a state change associated with said input data;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data;

transmitting, by said computing device to said data source organizations, said clarification inquiries data;

receiving, by said computing device from said data source organizations, response data associated with said clarification inquiries data;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

The present invention advantageously provides a simple method and associated system capable of retrieving information from multiple parties.

BRIEF DESCRIPTION OF THE DRAWINGS

FIG. 3 illustrates an example of a first table describing a modified analysis data file generated by the algorithm of FIG. 2, in accordance with embodiments of the present invention.

FIG. 4 illustrates an example of a second table describing a modified analysis data file generated by the algorithm of FIG. 2, in accordance with embodiments of the present invention.

DETAILED DESCRIPTION OF THE INVENTION

Figure 1:
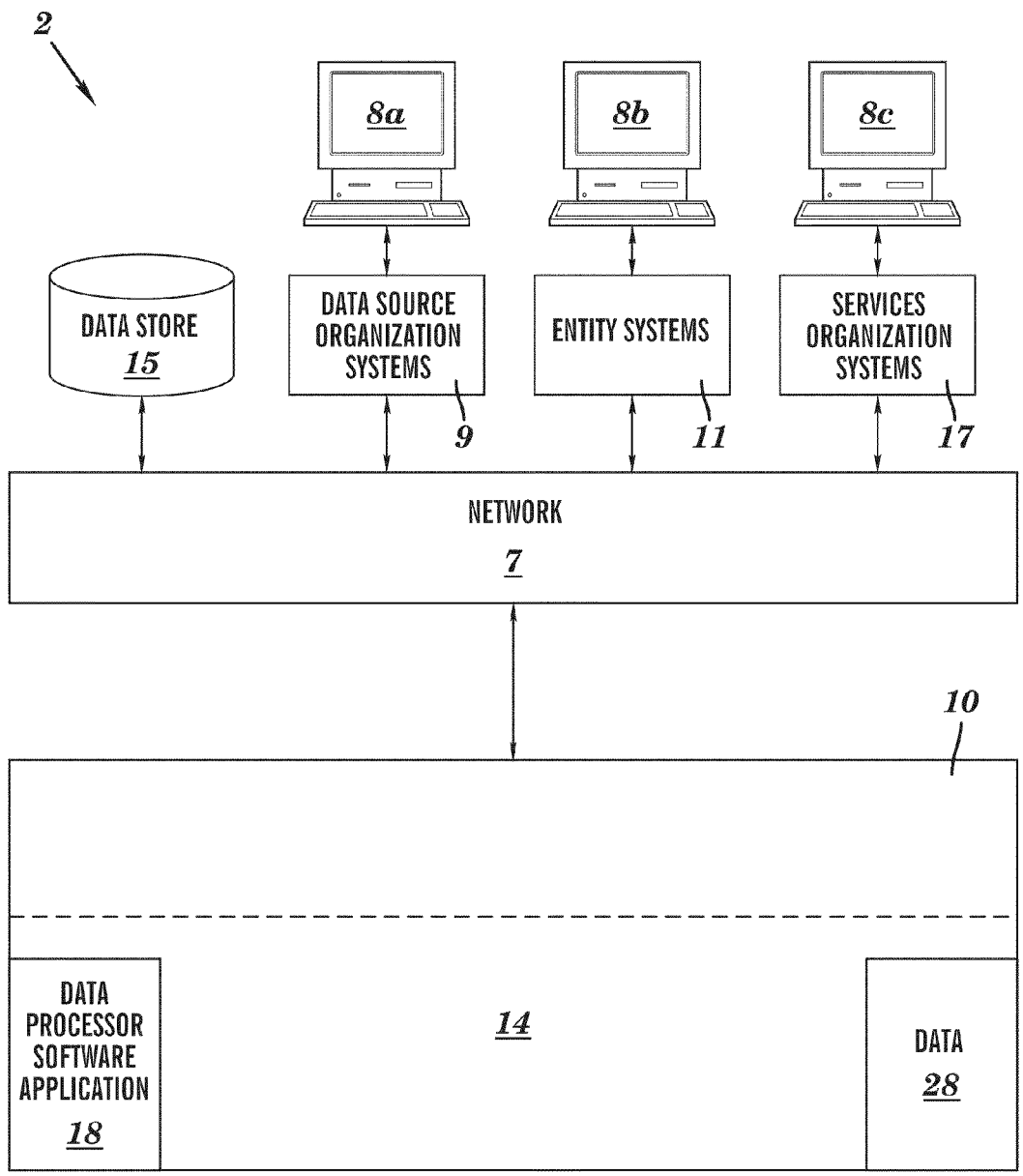
FIG. 1 illustrates a system for gathering and organizing data from multiple data source organizations, in accordance with embodiments of the present invention.

FIG. 1 illustrates a system 2 for gathering and organizing data from multiple data source organizations 9, in accordance with embodiments of the present invention. System 2 performs a process for allowing users to search for specified data associated with the users. For example, state health care services allow citizens to search for health care providers specific to their needs. In order to enable the process, a government health care agency communicates with two sets of organizations:

1. A set of government and medical departments that provide various health care data such as a location of hospitals and medical offices and lists of medical specialists. The set of government and medical departments are comprised by data source organizations (DSO).
2. A services organization (e.g., an I/T services organization) to develop software to aggregate and present the health care data to the users.

Each of the three process entities, (i.e., the government health care agency, the DSOs, and the services organization) access a data processor software application 18 (e.g., a health care data processor application (HCDPA)). The data processor software application 18 manages workflow between the three process entities to ultimately create a data source specification (DSS) document. Data processor software application 18 is a web-based software application, allowing login access to each of the process entities.

A DSS document is defined herein as a metadata file that describes a structure and semantic meaning of a data source. A data source may comprise a database(s) or a data service(s). A DSS document describes in a single file (e.g., a spreadsheet):

1. Fields or elements available in a data source.
2. Data types (e.g., numeric, string, etc) of the fields or elements.
3. Formats (e.g., string length, padding, etc) of the fields or elements.
4. Descriptions (e.g., this is a hospital name, this is a hospital street address, etc) of the fields or elements.

For example, a DSS may become a contract or interface between an entity (e.g., a data source provider such as, inter alia, a government agency, a private entity, etc) and an application component (e.g., data processor software application 18) that builds a data warehouse or repository (e.g., data store 15) of combined data sources. The application component (i.e., using the DSS) automates a process for ingesting an original data source and transforming its contents into a unified format in the data repository which will be directly useable in a final application. Over time, the DSS may be updated and refreshed.

System 2 of FIG. 1 comprises a data store 15, DSO systems 9, entity systems 11, and services organization systems 17 connected to a computing system 10 through a network 7. Additionally, I/O device(s) 8a...8c may be connected to each of DSO systems 9, entity systems 11, and services organization systems 17. I/O device 8a is used by an associated user for accessing DSO systems 9. I/O device 8b is used by an associated user for accessing entity systems 11. I/O device 8c is used by an associated user for accessing services organization systems 17. DSO systems 9 may comprise computer systems associated with any type of DSO. For example, a DSO may comprise an organization associated with health care facilities (e.g., hospitals, doctor offices, rehab centers, etc). Entity systems 11 may comprise computer systems associated with any type of entity. For example, an entity may comprise a government organization (e.g., associated with health care), a private company, etc. Services organization systems 17 may comprise computer systems associated with any type of services organization. For example, a services organization may comprise a software development organization, etc. I/O devices 8a . . . 8c may comprise any type of I/O device such as, inter alia, a notebook computer, a desktop computer, a personal digital assistant (PDA), etc. DSO systems 9, entity systems 11, and services organization systems 17 may comprise any type of computing systems including, inter alia, server computers, database computers, etc. Network 7 may comprise any type of network including, inter alia, a local area network, (LAN), a wide area network (WAN), the Internet, etc. Computing system 10 may comprise any type of computing system(s) including, inter alia, a personal computer (PC), a server computer, a database computer, etc. Computing system 10 comprises a memory system 14. Memory system 14 comprises data processor software application 18 and data 28 retrieved from DSO systems 9, entity systems 11, services organization systems 17, and data store 15. Data store 15 may comprise a single database or a plurality of databases.

Data processor software application 18 coordinates a process for gathering and organizing data from multiple data source organizations 9 in accordance with the following implementation example:

In this example, data processor software application 18 comprises a health care data processor (software) application (HCDPA), entity systems 11 comprising systems associated with a government health care agency (GHCA), and services organization systems 17 comprising systems associated with an IT service organization (ITSO). The HCDPA is a software application that automates a process for gathering and integrating health care data. The HCDPA manages the following six data structures:

1. A data source file layout worksheet.
2. A license/contract agreement.
3. A data dictionary.
4. An individual raw data file.
5. A clarification inquiry.
6. An IT entity analysis and recommendation.

A license/contract agreement is defined herein as a legal contract that covers all licensing agreements to obtain data from an individual data source organization. A data dictionary is defined herein as a glossary of terms regarding data elements in data files. A data dictionary is created by a data source organization. A raw data file is defined herein as a primary document starting in a raw format from a data source organization and is refined by all parties (i.e., GHCA, DSO, and ITSO) over the course of the process described with respect to FIG. 2, infra. A clarification inquiry is defined herein as a formal, trackable, documented question generated by the ITSO for the DSO to clear up errant or confusing elements in a data file.

The HCDPA performs the following process for gathering and processing data:

1. The HCDPA provides a secure Webpage (e.g., comprising a graphical user interface submit button) for the GHCA. When a user for the GHCA enables the submit button, the HCDPA will transmit an automatic email to each DSO. The email instructs each DSO to complete an online data source file layout worksheet and produce a data dictionary and a small representative set of sample data files.
2. In response, the HCDPA generates the following four data objects:
   A. A data source file layout worksheet.
   B. A data dictionary.
   C. A license/contract agreement.
   D. A sample data file.
3. Each DSO logs on to the HCDPA, fills out, and submits the following online forms:
   A. A data source file layout worksheet.
   B. A data dictionary.
   C. A sample data file upload.
4. Once all three forms are submitted, the HCDPA transmits an automatic notification email to the GHCA indicating that the data and the license/contract agreement is complete. The HCDPA moves the sample data file to a state of "For GHCA review". Additionally, the HCDPA moves the following three data objects to a "complete" state:
   A. The data source file layout worksheet.
   B. The data dictionary.
   C. The license/contract agreement.
5. The GHCA analyzes and prepares the data (i.e., generates a set of data files) for analysis by the ITSO. The HCDPA transmits a form (i.e., for uploading the set of data files) to the GHCA. Additionally, the form prompts the GHCA for data transformation requirements and crosswalk keys. When the GHCA submits the form, the HCDPA transmits an automatic email to the ITSO. The email states that the data is ready for an ITSO analysis. Additionally, the HCDPA moves the sample data file to a state of "For ITSO review".
6. The ITSO downloads the set of data files from the HCDPA and views the data transformation requirements and crosswalk keys online on the HCDPA system. The ITSO fills out an online form on the HCDPA system (i.e., for clarification inquiries) and enables a submit function. The HCDPA transmits an automatic email (i.e., associated with an inquiry(s)) to the DSO. The HCDPA moves the set of data files to a state of "For analysis and recommendations". Additionally, the HCDPA creates a clarification inquiry object and sets it to a state of "sent".
7. The DSO logs on to the HCDPA (system), opens a clarification inquiry form, provides an answer(s) in the clarification inquiry form, and submits the clarification inquiry form. The HCDPA notifies the ITSO that response(s) are ready. Additionally, the HCDPA sets the clarification inquiry object to a state of "answered".
8. The ITSO receives an email from the HCDPA and completes analysis and recommendations associated with the set of data files. The ITSO fills out and submits an analysis & recommendations form on the HCDPA. The HCDPA transmits an automatic notification email to the GHCA, which acts on the analysis and recommendations. Additionally, the HCDPA also creates an analysis and recommendations data object and sets the object to a state of "sent".

Figure 2:
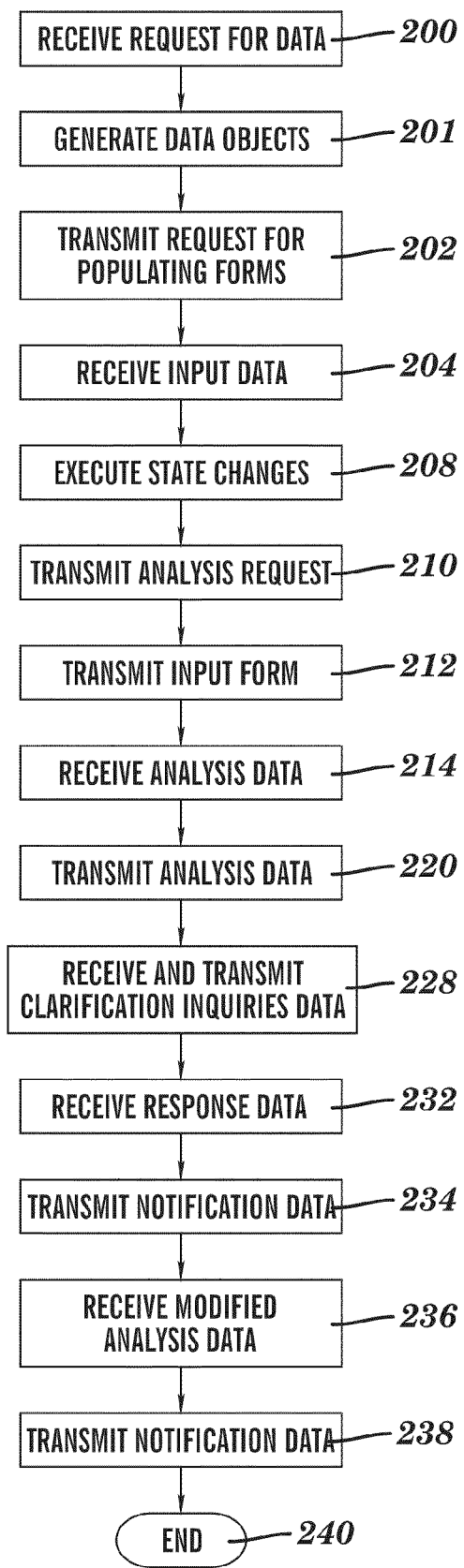
FIG. 2 illustrates a flowchart describing an algorithm used by the system of FIG. 1 for gathering and organizing data from multiple data source organizations, in accordance with embodiments of the present invention.

FIG. 2 illustrates a flowchart describing an algorithm used by system 2 of FIG. 1 for gathering and organizing data from multiple data source organizations, in accordance with embodiments of the present invention. In step 200, a computing device (e.g., computing system 10 in FIG. 1) receives from a first entity (e.g., a government healthcare agency), a first request for data. In step 201, the computing device generates worksheet data objects. For example, input data may comprise dictionary data, license/contract agreement data (e.g., associated with a plurality of original data sources providing data to the data source organizations), and sample data files data. The worksheet data objects may comprise a data source file worksheet data object, a data dictionary worksheet data object, a sample data files data worksheet data object, and a license/contract agreement data worksheet data object. In step 202, the computing device transmits (i.e., to a plurality of data source organizations in response to the first request) a second request for populating a plurality of online forms comprising the worksheet data objects. In step 204, the computing device receives (i.e., from the data source organizations in response to the second request) input data associated with (and for populating) the online forms. In step 208, the computing device executes a state change(s) associated with the input data. In step 210, the computing device transmits (i.e., to said first entity) first notification data requesting analysis of the input data. In step 212, the computing device transmits (i.e., to the first entity) an input form for uploading results of the analysis of the input data. In step 214, the computing device receives (i.e., from the first entity in response to the input form) analysis data files indicating the results of the analysis of the input data. In step 220, the computing device transmits (i.e., to an IT service organization) the analysis data files and data transformation requirements. In step 228, the computing device receives (i.e., from the IT service organization) clarification inquiries data and transmits the clarification inquiries data to the data source organizations. In step 232, the computing device receives (i.e., from the data source organizations) response data associated with the clarification inquiries data. In step 234, the computing device transmits (i.e., to the IT service organization) notification data requesting analysis of the analysis data files. In step 236, the computing device receives (i.e., from the IT service organization) modified analysis data files associated with the analysis data files. In step 238, the computing device transmits (i.e., to the first entity) second notification data indicating results of the modified analysis data files and the process is terminated in step 240.

FIG. 3 illustrates an example of a table 300 describing a modified analysis data file generated by the algorithm of FIG. 2, in accordance with embodiments of the present invention. Table 300 comprises nursing home charge data. The nursing home charge data comprises data (i.e., associated with nursing homes) such as a facility name, a room rate, a leave rate, etc. Table tracks mismatches of ID numbers from multiple data sources.

FIG. 4 illustrates an example of a table 400 describing a modified analysis data file generated by the algorithm of FIG. 2, in accordance with embodiments of the present invention. Table 400 illustrates facility A care data. Table 400 comprises elements such as: total employees, whether facility A provides counseling (Y or N), home health aides (Y of N), etc.

Figure 5:
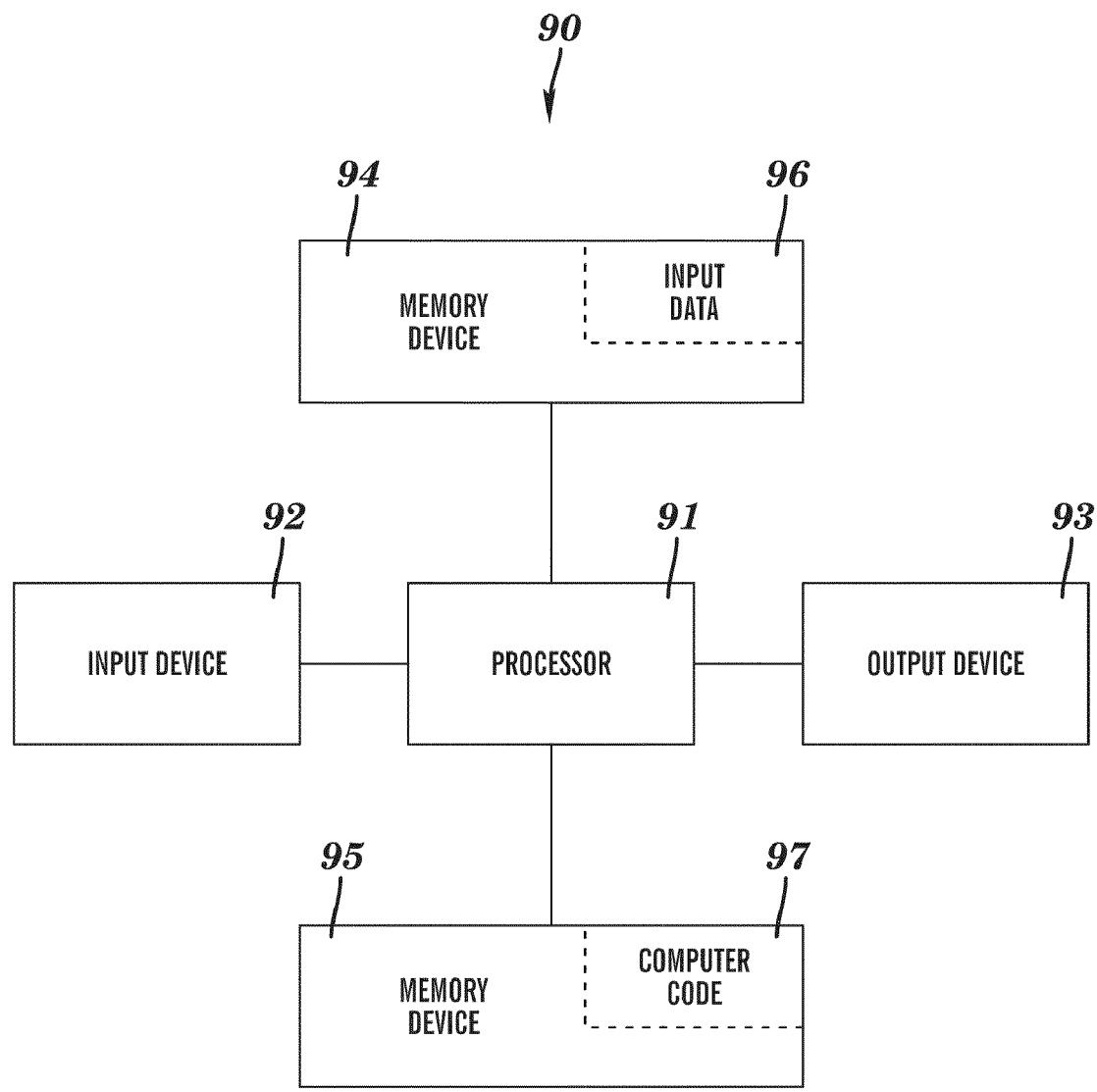
FIG. 5 illustrates a computer apparatus used for gathering and organizing data from multiple data source organizations, in accordance with embodiments of the present invention.

FIG. 5 illustrates a computer apparatus 90 (e.g., computing system 10 of FIG. 1) used for gathering and organizing data from multiple data source organizations, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithm of FIG. 2) for gathering and organizing data from multiple data source organizations. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 5) may comprise the algorithm of FIG. 2 and may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device).

Still yet, any of the components of the present invention could be created, integrated, hosted, maintained, deployed, managed, serviced, etc. by a service provider who offers to gather and organize data from multiple data source organizations. Thus the present invention discloses a process for deploying, creating, integrating, hosting, maintaining, and/or integrating computing infrastructure, comprising integrating computer-readable code into the computer system 90, wherein the code in combination with the computer system 90 is capable of performing a method for gathering and organizing data from multiple data source organizations. In another embodiment, the invention provides a business method that performs the process steps of the invention on a subscription, advertising, and/or fee basis. That is, a service provider, such as a Solution Integrator, could offer to gather and organize data from multiple data source organizations. In this case, the service provider can create, maintain, support, etc. a computer infrastructure that performs the process steps of the invention for one or more customers. In return, the service provider can receive payment from the customer(s) under a subscription and/or fee agreement and/or the service provider can receive payment from the sale of advertising content to one or more third parties.

While FIG. 5 shows the computer system 90 as a particular configuration of hardware and software, any configuration of hardware and software, as would be known to a person of ordinary skill in the art, may be utilized for the purposes stated supra in conjunction with the particular computer system 90 of FIG. 5. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A data retrieval method comprising:
receiving, by a computing device from a first entity, a first request for data;
transmitting, by said computing device to a plurality of data source organizations in response to said first request, a second request for populating a plurality of online forms;
receiving, by said computing device from said data source organizations in response to said second request, input data associated with said online forms, wherein said input data comprises dictionary data, license/contract agreement data, and sample data files data, wherein said license/contract agreement is associated with a plurality of original data sources providing data to said plurality of data source organizations;

generating by said computing device from said input data, a data source file worksheet data object, a data dictionary worksheet data object, a sample data files data worksheet data object, and a license/contract agreement data worksheet data object;

populating, by said computing device, said plurality of online forms with said data source file worksheet data object, said data dictionary worksheet data object, said sample data files data worksheet data object, and said license/contract agreement data worksheet data object;

executing, by a computer processor of said computing device, a first state change associated with said data source file worksheet data object, said data dictionary worksheet data object, and said license/contract agreement data worksheet data object, wherein said first state change indicates a completed state for said plurality of online forms;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data comprising a trackable question associated with errant elements within said input data;

generating, by said computing device, a clarification inquiries data object from said clarification inquiries data;

transmitting, by said computing device to said IT service organization, said clarification inquiries data object;

receiving, by said computing device from said data source organizations, response data associated with said clarification inquiries data;

executing, by said computer processor in response to said receiving said response data, a second state change associated with said clarification inquiries data object, wherein said second state change indicates an answered state for said clarification inquiries data object;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

2. The method of claim 1, wherein said transmitting said first notification data comprises transmitting said license/contract agreement data to said first entity.

3. The method of claim 1, further comprising:
generating, by said computing device, an analysis and recommendation data object associated with said analysis data files and recommendations from said IT service organization.

4. The method of claim 1, wherein said plurality of data source organizations comprise government health care data source organizations, wherein said input data comprises health care data, and wherein said first entity comprises a government healthcare agency.

5. The method of claim 1, wherein said license/contract agreement data comprises a contract between a government agency and a software application component.

6. A computing device comprising a processor coupled to a computer-readable memory unit, said memory unit comprising instructions that when executed by the processor implement a data retrieval method, said method comprising:

receiving, by said computing device from a first entity, a first request for data;

generating by said computing device, a data source file worksheet data object, a data dictionary worksheet data object, a sample data files data worksheet data object, and a license/contract agreement data worksheet data object;

transmitting, by said computing device to a plurality of data source organizations in response to said first request, a second request for populating a plurality of online forms;

receiving, by said computing device from said data source organizations in response to said second request, input data associated with said online forms, wherein said input data comprises dictionary data, license/contract agreement data, and sample data files data, wherein said license/contract agreement is associated with a plurality of original data sources providing data to said plurality of data source organizations;

generating by said computing device from said input data, a data source file worksheet data object, a data dictionary worksheet data object, a sample data files data worksheet data object, and a license/contract agreement data worksheet data object;

populating, by said computing device, said plurality of online forms with said data source file worksheet data object, said data dictionary worksheet data object, said sample data files data worksheet data object, and said license/contract agreement data worksheet data object;

executing, by processor of said computing device, a first state change associated with said data source file worksheet data object, said data dictionary worksheet data object, and said license/contract agreement data worksheet data object, wherein said first state change indicates a completed state for said plurality of online forms;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data comprising a trackable question associated with errant elements within said input data;

generating, by said computing device, a clarification inquiries data object from said clarification inquiries data;

transmitting, by said computing device to said IT service organization, said clarification inquiries data object;

receiving, by said computing device from said data source organizations, response data associated with said clarification inquiries data;

executing, by said processor in response to said receiving said response data, a second state change associated with said clarification inquiries data object, wherein said second state change indicates an answered state for said clarification inquiries data object;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

7. The computing device of claim 6, wherein said transmitting said first notification data comprises transmitting said license/contract agreement data to said first entity.

8. The computing device of claim 6, wherein said method further comprises:

generating, by said computing device, an analysis and recommendation data object associated with said analysis data files and recommendations from said IT service organization.

9. The computing device of claim 6, wherein said plurality of data source organizations comprise government health care data source organizations, wherein said input data comprises health care data, and wherein said first entity comprises a government healthcare agency.

10. A computer program product, comprising a computer readable memory device comprising a computer readable program code embodied therein, said computer readable program code adapted to implement a data retrieval method within a computing device comprising a computer-readable memory unit, said method comprising:

receiving, by said computing device from a first entity, a first request for data;

generating by said computing device, a data source file worksheet data object, a data dictionary worksheet data object, a sample data files data worksheet data object, and a license/contract agreement data worksheet data object;

transmitting, by said computing device to a plurality of data source organizations in response to said first request, a second request for populating a plurality of online forms;

receiving, by said computing device from said data source organizations in response to said second request, input data associated with said online forms, wherein said input data comprises dictionary data, license/contract agreement data, and sample data files data, wherein said license/contract agreement is associated with a plurality of original data sources providing data to said plurality of data source organizations;

generating by said computing device from said input data, a data source file worksheet data object, a data dictionary worksheet data object, a sample data files data worksheet data object, and a license/contract agreement data worksheet data object;

populating, by said computing device, said plurality of online forms with said data source file worksheet data object, said data dictionary worksheet data object, said sample data files data worksheet data object, and said license/contract agreement data worksheet data object;

executing, by a computer processor of said computing device, a first state change associated with said data source file worksheet data object, said data dictionary worksheet data object, and said license/contract agreement data worksheet data object, wherein said first state change indicates a completed state for said plurality of online forms;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data comprising a trackable question associated with errant elements within said input data;

generating, by said computing device, a clarification inquiries data object from said clarification inquiries data;

transmitting, by said computing device to said IT service organization, said clarification inquiries data object;

receiving, by said computing device from said data source organizations, response data associated with said clarification inquiries data;

executing, by said computer processor in response to said receiving said response data, a second state change associated with said clarification inquiries data object, wherein said second state change indicates an answered state for said clarification inquiries data object;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

11. The computer program product of claim 10, wherein said transmitting said first notification data comprises transmitting said license/contract agreement data to said first entity.

12. The computer program product of claim 10, wherein said method further comprises:

generating, by said computing device, an analysis and recommendation data object associated with said analysis data files and recommendations from said IT service organization.

13. The computer program product of claim 10, wherein said plurality of data source organizations comprise government health care data source organizations, wherein said input data comprises health care data, and wherein said first entity comprises a government healthcare agency.

14. A process for supporting computer infrastructure, said process comprising providing at least one support service for at least one of creating, integrating, hosting, maintaining, and deploying computer-readable code in a computing device comprising a computer-readable memory unit, wherein the code in combination with the computing device is capable of performing a data retrieval method, said method comprising:

receiving, by said computing device from a first entity, a first request for data;

generating by said computing device, a data source file worksheet data object, a data dictionary worksheet data object, a sample data files data worksheet data object, and a license/contract agreement data worksheet data object;

transmitting, by said computing device to a plurality of data source organizations in response to said first request, a second request for populating a plurality of online forms;

receiving, by said computing device from said data source organizations in response to said second request, input data associated with said online forms, wherein said input data comprises dictionary data, license/contract agreement data, and sample data files data, wherein said license/contract agreement is associated with a plurality of original data sources providing data to said plurality of data source organizations;

generating by said computing device from said input data, a data source file worksheet data object, a data dictionary worksheet data object, a sample data files data worksheet data object, and a license/contract agreement data worksheet data object;

populating, by said computing device, said plurality of online forms with said data source file worksheet data object, said data dictionary worksheet data object, said sample data files data worksheet data object, and said license/contract agreement data worksheet data object;

executing, by a computer processor of said computing device, a first state change associated with said data source file worksheet data object, said data dictionary worksheet data object, and said license/contract agreement data worksheet data object, wherein said first state change indicates a completed state for said plurality of online forms;

transmitting, by said computing device to said first entity, first notification data requesting analysis of said input data;

transmitting, by said computing device to said first entity, an input form for uploading results of said analysis of said input data;

receiving, by said computing device from said first entity in response to said transmitting said input form, analysis data files indicating said results of said analysis of said input data;

transmitting, by said computing device to an IT service organization, said analysis data files and data transformation requirements;

receiving, by said computing device from said IT service organization, clarification inquiries data comprising a trackable question associated with errant elements within said input data;

generating, by said computing device, a clarification inquiries data object from said clarification inquiries data;

transmitting, by said computing device to said IT service organization, said clarification inquiries data object;

receiving, by said computing device from said data source organizations, response data associated with said clarification inquiries data;

executing, by said computer processor in response to said receiving said response data, a second state change associated with said clarification inquiries data object, wherein said second state change indicates an answered state for said clarification inquiries data object;

transmitting, by said computing device to said IT service organization, notification data requesting analysis of said analysis data files;

receiving, by said computing device from said IT service organization, modified analysis data files associated with said analysis data files; and transmitting, by said computing device to said first entity, second notification data indicating results of said modified analysis data files.

* * * * *